United States Patent [19]

Eastman et al.

[11] Patent Number: 5,413,722
[45] Date of Patent: May 9, 1995

[54] BIOCIDAL PROCESS UTILIZING DECYLNONYL- AND DECYLISONONYL DIMETHYLAMMONIUM COMPOUNDS

[75] Inventors: David W. Eastman, Riverdale; Kenneth J. Iandoli, Hawthorne; Chuen-Ing J. Tseng, Edison, all of N.J.

[73] Assignee: Lonza Inc., Fair Lawn, N.J.

[21] Appl. No.: 157,956

[22] Filed: Nov. 24, 1993

Related U.S. Application Data

[62] Division of Ser. No. 790,775, Nov. 12, 1991, Pat. No. 5,290,805.

[51] Int. Cl.$^6$ ............................ C02F 1/50; A01N 33/12
[52] U.S. Cl. ................................... 210/755; 210/764; 504/158; 514/642; 564/291
[58] Field of Search ................. 210/755, 764; 514/642; 564/291, 295; 504/158

[56] References Cited

U.S. PATENT DOCUMENTS

| | | | |
|---|---|---|---|
| 3,754,033 | 8/1973 | Shay et al. | 424/329 |
| 4,444,790 | 4/1984 | Green et al. | 424/329 |
| 4,450,174 | 5/1984 | Green et al. | 424/329 |
| 5,015,395 | 5/1991 | Muia et al. | 210/755 |
| 5,062,967 | 11/1991 | Muia et al. | 210/755 |

FOREIGN PATENT DOCUMENTS

| | | |
|---|---|---|
| 33748/68 | 10/1971 | Australia . |
| 1460037 | 10/1966 | France . |
| 719617 | 10/1950 | United Kingdom . |
| 650304 | 2/1951 | United Kingdom . |

OTHER PUBLICATIONS

Ramsay et al., "Effects of Non-Oxidizing Biocides on Adult *Corbicula Fluminea*," Oct. 17, 1988.

*Primary Examiner*—Thomas Wyse
*Attorney, Agent, or Firm*—Darby & Darby

[57] ABSTRACT

Quaternary ammonium compounds having the structural formula:

$$\left[ \begin{array}{c} CH_3 \\ | \\ decyl-N-R \\ | \\ CH_3 \end{array} \right]^+ X^-$$

wherein X is chloride, bromide, iodide or alkyl carboxylate having a $C_1$–$C_{18}$ alkyl radical, and R is n-nonyl or isononyl. The disclosed compounds were found to be non-toxic, low foaming, effective biocides in treatment methods for controlling bacteria, algae and molluscs in aqueous systems.

6 Claims, 6 Drawing Sheets

BIOCIDAL PROCESS UTILIZING DECYLNONYL- AND DECYLISONONYL DIMETHYLAMMONIUM COMPOUNDS

This is a division of application Ser. No. 07/790,775, filed Nov. 12, 1991, now U.S. Pat. No. 5,290,805, issued Mar. 1, 1994.

FIELD AND BACKGROUND OF THE INVENTION

Quaternary ammonium compounds have been widely used as bactericides, algicides and molluscicides to treat circulating or static bodies of water. The estimated current market for quaternary ammonium compounds in the water treatment of cooling towers, pool, and spa industries is approximately 15 to 16 million pounds per year. These markets have been traditionally served by higher alkyl and dialkyl quaternary ammonium compounds as it is known that such compounds possess potent biocidal properties.

Higher alkyl and dialkyl quaternary ammonium compounds known in the art, however, suffer from one or more deficiencies which include a limited spectrum of biocidal activity, high foaming characteristics, inherent toxicity, and disagreeable odor production. Moreover, it is known that the beneficial biocidal effects of these agents are substantially inhibited when used in hard water. Hence, the aforementioned deficiencies are important factors in limiting the greater usage of quaternaries as biocides in practical water treatment.

For example, dioctyldimethylammonium chloride has low foam, but has high toxicity and poor bactericidal and algicidal properties. Didecyldimethylammonium chloride, in contrast, is a highly effective bactericide and algicide with low toxicity, but has high foam. Similarly, diisodecyldimethyl ammonium chloride disclosed in U.S. Pat. Nos. 4,444,790 and 4,450,174 causes eye irritation and odor problems. The high foaming characteristic of conventional dialkyl quaternaries is an undesirable feature in their use as algicides in recirculating cooling water systems.

Various quaternary ammonium compounds, including dioctyldimethylammonium chloride, have been used as molluscicides for controlling molluscs, e.g. zebra mussels and asian clams, infestation of fresh water supplies (see, for example, U.S. Pat. No. 5,015,395 and references therein). However, many of these quaternaries suffer from at least one of the aforementioned deficiencies and thus do not offer an effective means for controlling mollusc growth.

Zebra mussels (*Dreissena polymorpha*) have recently been discovered in various lakes and rivers of the Midwest and Northeast regions of the United States. For example, Zebra mussel contamination was found in the Great Lakes of North America which serve as the main fresh water supply for domestic municipal, utility, and industrial use in this region. The resulting economic costs to industry and fishing in this region alone was estimated to be about $500 million in 1990.

Because of their propensity to reproduce quickly and their ability to affix themselves onto any hard surface in contact with an aqueous system in which they are present, zebra mussels are particularly troublesome in municipal water treatment plants and industrial water systems as zebra mussels can foul water intake piping and process equipment. Accordingly, there is a need for safe and effective molluscicides for practical water treatment to inhibit zebra mussel growth.

Surprisingly, it has now been discovered that decylnonyl- and decylisononyldimethylammonium compounds, especially decylnonyldimethylammonium chloride and decylisononyldimethylammonium chloride, exhibit a superior range of bactericidal, algicidal, and molluscicidal properties with virtually none of the undesirable foaming properties and toxicities commonly found in quaternary ammonium compounds currently in use. In particular, the quaternary ammonium compounds of the invention are especially effective in inhibiting the growth of algae such as *Chlorella pyrenoidosa*, Mustard Algae and *Phormidium luridum*.

Decylnonyldimethylammonium chloride and decylisononyldimethylammonium chloride, individually or as mixtures thereof, therefore, have enormous potential utility in the treatment of pools, spas, and recirculating and stationary cooling towers as well as in household disinfectant products and other industrial biocide market areas.

SUMMARY OF THE INVENTION

The present invention relates to a method for treating water and to biocidal quaternary ammonium compounds having the structural formula:

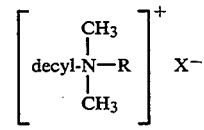

wherein X is chloride, bromide, iodide, or alkyl carboxylate anions having a $C_1$–$C_{18}$ alkyl radical, and R is n-nonyl or isononyl. The quaternaries of the present invention are highly efficacious as bactericides, algicides, and molluscicides which have low foaming properties and toxicity, relative to conventional quaternaries, when employed at effective concentrations in water.

The quaternaries of the invention are highly efficacious biocides in water with calcium hardness, expressed as $CaCO_3$, up to at least 400 ppm even in the presence of organic soil.

Accordingly, it is an object of the invention to provide decylnonyl- and decylisononyldimethylammonium compounds, particularly decylnonyldimethylammonium chloride (decylnonyl DMAC) and decylisononyldimethylammonium chloride (decylisononyl DMAC), as effective bactericides, algicides, and molluscicides for use in water treatment. The quaternary ammonium compounds of the invention are especially effective in inhibiting the growth of algae such as *Chlorella pyrenoidosa* Mustard Algae and *Phormidium luridum*. The compounds are safe to use, e.g. non-irritating to eyes, and do not produce offensive odors when effective concentrations are employed in water.

It is another object of the invention to provide safe, effective quaternary ammonium compounds which produce virtually no foaming when added to a circulating body of water. Such compounds are especially useful in pools, spas, and recirculating water towers where foam production is undesirable.

It is yet another object of the invention to provide a method to inhibit the growth of microbes and algae in water.

It is a further object of the invention to provide a method to inhibit the growth of molluscs, especially zebra mussels and asian clams, in water.

These and other objects of the invention will be apparent in light of the detailed description below.

Figure 1:
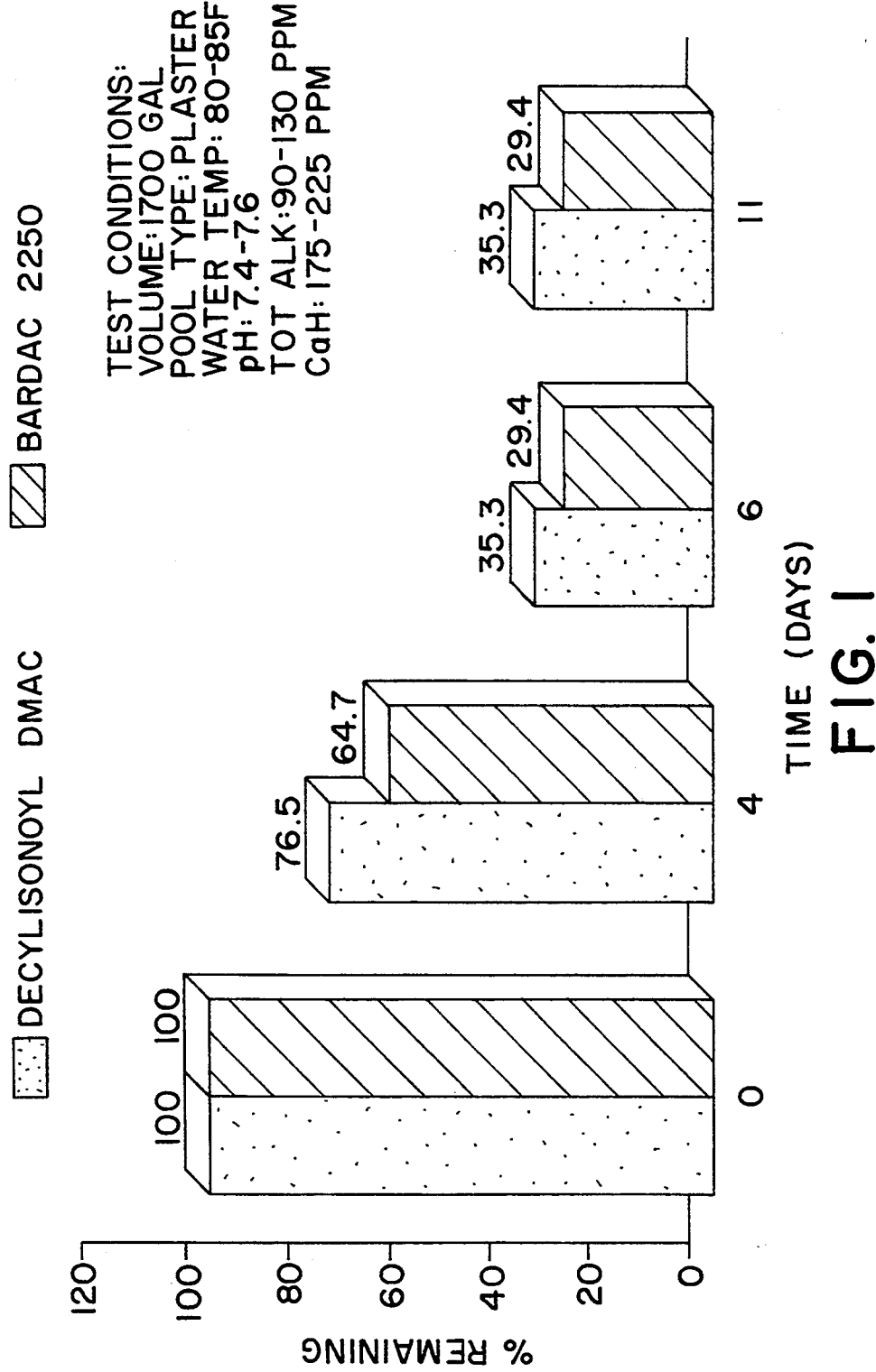
FIG. 1 illustrates the half-life of decylisononyl DMAC and commercial Bardac 2250 in a circulating body of water.

The chemical compositions and suppliers of the commercial biocides cited in the aforementioned Figures, for comparison with compounds of the invention, are summarized below:

| Biocides | Supplier | Chemical Composition |
| --- | --- | --- |
| Bardac 2250 | Lonza | Didecyldimethylammonium Chloride |
| Barquat MB-50 | Lonza | N-Alkyl ($C_{14}$, 50%; $C_{12}$, 40%; $C_{16}$, 10%) dimethylbenzylammonium Chloride |
| Bio-Quat 50-40 | BioLab | N-Alkyl ($C_{14}$, 50%; $C_{12}$, 40%; $C_{16}$, 10%) dimethylbenzylammonium Chloride |
| BTC 99 | Stepan | Diisodecyldimethylammonium Chloride |
| Buckman WSCP | Buckman Laboratories | Poly[oxyethylene (dimethylimino) ethylene (dimethylimino) ethylene dichloride] |
| Bio-Quat 50-28 | BioLab | N-Alkyl ($C_{14}$, 95%; $C_{12}$, 3%; $C_{16}$, 2%) dimethylbenzylammonium Chloride |

DETAILED DESCRIPTION OF THE INVENTION

The dialkyldimethyl quaternary ammonium compounds of the present invention are decylnonyl- and decylisononyl dimethylammonium compounds, especially decylnonyl DMAC and decylisononyl DMAC. These quaternaries may be prepared by any known process. See, for example, U.S. Pat. Nos. 3,754,033 and 4,450,174 as well as A. W. Ralston, et al., *J. Org. Chem.,* vol. 13, p. 186 (1948).

For example, the compounds of the present invention may be prepared by the classical alkylation reaction of a tertiary amine with a primary alkyl halide. The tertiary amine may be prepared by the alkylation of a secondary amine with a primary alkyl halide or by two successive alkylations of a primary amine in which the alkyating agents may be the same or different primary alkyl halides. In general, the quaternization of dialkylmethylamines with methyl chloride gives higher yields than the quaternization of alkyldimethylamides with alkyl halides.

The anions in the dialkyldimethyl quaternary ammonium compounds of the present invention may be chloride, bromide, iodide and alkyl carboxylates having a $C_1$–$C_{18}$ alkyl radical. For example, decylisononyl DMAB may be prepared by the reaction of decylisononylmethylamine with methyl bromide. Decylisononyl dimethylammonium iodide may be prepared by the reaction of decylisononylmethylamine with methyl iodide. Decylisononyl DMAA may be prepared by passing decylisononyl DMAC through an ion exchange resin, such as IR 401 ion exchange resin produced by Rohm & Hass Company, which has been surface treated with acetate as anions.

Normal nonyl, isononyl and decyl alcohols may be converted to their respective primary alkyl halides, e.g. alkyl chlorides, for use in amination reactions. For example, alkyl chlorides are generally prepared by reacting the primary alcohol with conventional chlorinating agents, i.e. thionyl chloride and phosphorus trichloride. The isomeric distribution of the nonyl, isononyl and decyl chlorides will depend on the starting alcohol distribution.

Normal nonyl alcohol with no branching may be obtained from Givaudan (Clifton, N.J., U.S.A.). Normal nonyl alcohol may also be obtained by fractional distillation of Exxal L911 (Exxon Chemical U.S.A.; Baton Rouge, La., U.S.A.) to separate the $C_9$ fraction. Exxal L911 is a surfactant grade alcohol consisting of a 1:1 ratio of nonyl and undecyl ($C_{11}$) alcohols. The $C_9$ fraction has about 25% branching on the beta-carbon.

Normal nonyl alcohol may also be obtained by fractional distillation of Neodol 91 (Shell Chemical Company; Geismar, La., U.S.A.). Neodol 91 contains a 1:2:2 ratio of nonyl, decyl and undecyl alcohols. The $C_9$ fraction has about 18% branching on the beta-carbon.

Isononyl alcohol is manufactured by catalytic hydroformulation of higher olefin feed stocks. The isomer distribution and carbon numbers are controlled by distillation. The major branched primary alcohol isomers in, for example, Exxal 9 (Exxon Chemical U.S.A.; Baton Rouge, La., U.S.A.) are dimethyl-1-heptanols and methyl-1-octanols with about 20% of primary $C_{10}$ alcohols.

The quaternaries of the present invention are highly effective bactericides, algicides and mollusicides both individually or in admixtures.

The amount of quaternary compounds that may be used in water is dependent on the particular application. In pools, spas and other stationary bodies of water, the amount of quaternary dissolved in water is broadly between about 0.5 and about 10 ppm, preferably between about 1 and about 5 ppm.

For circulating bodies of water such as recirculating cooling towers, air washers, and once-through cooling system, the concentration of quaternary dissolved in water is broadly between about 0.5 and about 100 ppm, preferably between about 1 and about 50 ppm.

Maximum biocidal and algicidal effect of the quaternaries of the present invention is dependent on a number of factors which include operational pH, temperature, hardness of the water, organic contaminants, and anion additives. For example, the pH of the water should be broadly between about 4 and about 10, preferably between about 7 and about 9.

The quaternaries of the present invention can be added to the aqueous system being treated in any conventional manner and at any point best suited to provide ready dissolution and rapid distribution of the compounds in the aqueous system being treated. Various formulations of the present quaternaries which facilitate its dissolution in water may be prepared in accordance with known methods. Any form of the present quaternaries can be used, including but not limited to emulsions, dry forms and solutions containing 0-100% alcohol, e.g. ethanol, with the balance being water. Also, other water treatment agents can be added to the system being treated in conjunction with the present quaternaries. For example, other biocides, surfactants, scale or corrosion inhibitors, dispersants, flocculants or clarification aids can be used with the quaternaries of the present invention.

The following examples illustrate the invention without limiting its scope.

Example 1: Synthesis of Decylisononyldimethylammonium Chloride a. Amination Reaction to Form a Tertiary Amine Isononyl Chloride+Decylmethylamine—>Decylisononylmethylamine A mixture of 300 moles of decylmethylamine, 300 moles of isononyl chloride and 350 moles of 50% caustic soda, contained in a 50 gallon reactor, was heated for 6 hours at a temperature of 190° C. The organic mixture was cooled, washed with water and further purified by fractional distillation. The amination process afforded a yield of 83% decylisononylmethylamine. When nonyl chloride is used instead of isononyl chloride, the product is decylnonylmethylamine.

b. Quaternization of a Tertiary Amine with Methyl Chloride

Decylisononylmethylamine+Methyl—>-Decylisononyldimethyl Chloride Ammonium Chloride 150 moles of decylisononyldimethylamine, contained in an autoclave, is mixed with ethanol and/or water as solvent. Thereafter, 165 moles of methyl chloride gas is pumped into the autoclave and the contents are heated at about 85°-105° C. for about 4-5 hours. Decylisononyldimethylammonium chloride, the quaternary ammonium salt product, is left in solution, its concentration being about 50-90%, depending upon the quantity of solvent used in the reaction. The concentration of ethanol in the quaternary ammonium salt product is 0-50%, preferably between 0-20%.

When decylnonylmethylamine is used instead of decylisononylmethylamine, the product is decylnonyldimethylammonium chloride. Similarly, when methyl bromide or methyl iodide are used instead of methyl chloride, the products are decylisononyldimethylammonium bromide and decylisononyldimethylammonium iodide, respectively.

Example 2: Evaluation of Algicidal Efficacy

The test organisms used in this example were Mustard Algae and *Phormidium luridum*. The test method employed is described below.

The microdilution procedure was used for the determination of MIC (minimum inhibitory concentration). Aliquots of 100 microliters of sterile Difco Algae broth was added to wells of flat bottom 96 wells tissue culture plate. To the first well, 100 microliter of a solution containing 256 ppm active concentration of test algicide dissolved in distilled water was added, mixed with the broth, and 100 microliter was transferred to the adjacent well to give 2-fold serial dilutions.

The test organisms used as inoculum were grown in algae broth for 4-5 weeks. The cultures were vigorously vortexed to disperse the algae and the $OD_{600}$ was noted ($OD_{600}$ of 0.178 for Phormidium is equivalent to $1.63 \times 10^8$ cells/ml by direct microscopic count and $OD_{600}$ of 0.073 for mustard algae is equivalent to $2.1 \times 10^6$ cells by direct microscopic count). The inoculum was diluted in algae broth to give final concentration of $3.0 \times 10^5$ cells/mi. 100 microliters of inoculum was added to wells which resulted in a final concentration of 64 ppm of algicide in the first well. The plates were incubated at room temperature in a moist environmental chamber with the light and dark cycle set for 16 and 8 hours respectively. Results were noted as positive or negative growth for various concentrations at 7, 14, 21 days. The lowest concentration that inhibited the growth of microorganism was reported as the MIC.

Figure 2:
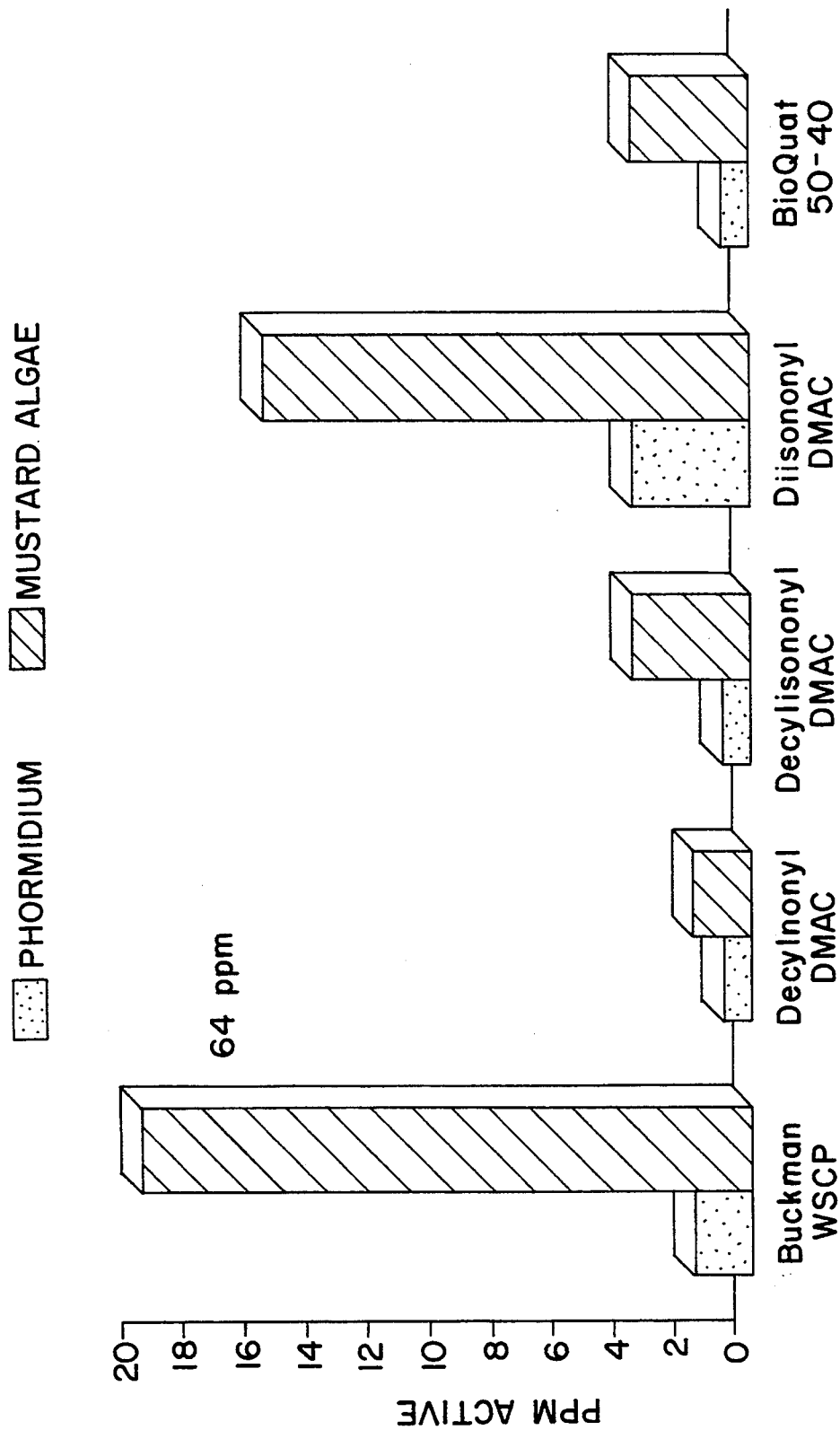
FIG. 2 illustrates the minimum inhibitory concentration (MIC) required to inhibit growth of Phormidium and mustard algae. Decylnonyl DMAC and decylisononyl DMAC are compared to diisononyl DMAC and the commercial quaternaries Buckman WSCP and Bio-Quat 50-40.

The MIC values, in ppm active concentrations, for various algicides tested are shown in FIG. 2 and in Table 1.

TABLE 1

| ALGICIDAL EFFICACY STUDY-MIC* | | | | |
|---|---|---|---|---|
| COMPOUND NAME | MIC PHORMIDIUM | | MIC MUSTARD ALGAE | |
| | 7 DAY | 21 DAY | 7 DAY | 21 DAY |
| Decylnonyl DMAC | 0.5 | 1 | 2 | 2 |
| Decylisononyl DMAC | 0.5 | 1 | 2 | 4 |
| Diisononyl DMAC | 2 | 4 | 4 | 16 |
| Buckman WSCP | 1 | 2 | 64 | 64 |
| Bio-Quat 50-40 | 1 | 1 | 4 | 4 |
| Bio-Quat 50-28 | 1 | 1 | 4 | 4 |

*Concentration in ppm active biocides

Commercial algicides Bio-Quat 50-40 and Bio-Quat 50-28 (BioLab, Decatur, Ga.) showed identical MICs on days 7, 14, and 21. A one or two dilution higher MIC was observed on day 21 as compared to day 7 for decylnonyl DMAC, decylisononyl DMAC and diisononyl DMAC. Buckman WSCP (Buckman Laboratories, Memphis, Tenn.) was not inhibitory at the concentrations tested (64 to 0.13 ppm). The tube dilution assay to determine MICs showed identical results with the microtiter system at 21 days.

Example 3: EPA Pure Culture Algicidal Efficacy Test

The following quaternary ammonium compounds—decylnonyl DMAC, nonylisononyl DMAC, dinonyl DMAC, decyl-2-ethylhexyl DMAC, decyloctyl DMAC, decylisooctyl, decylisononyl DMAC, and diisononyl DMAC—have been tested for algicidal efficacy and the results were compared with Buckman WSCP and BTC-99. Two algae cultures, *Chlorella pyrenoidosa* and *Phormidium luridum*, were used in this study.

Figure 4:
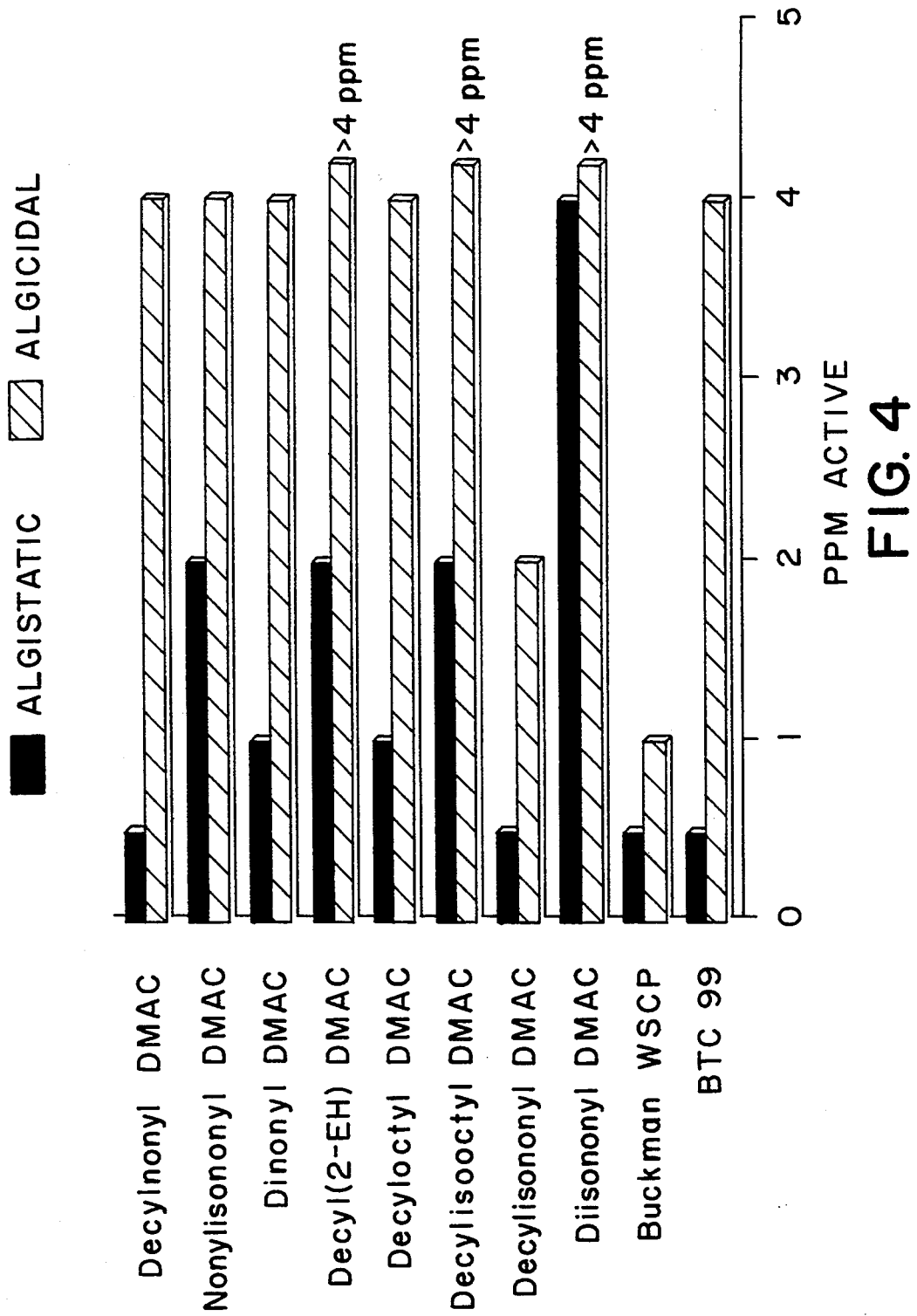
FIG. 4 illustrates an EPA pure culture test against *Chlorella pyrenoidosa* (algae) at a concentration of $3.0 \times 10^5$ cells/ml. Decylnonyl DMAC and decyisononyl DMAC are compared to diisononyl DMAC and commercial quaternaries such as Buckman WSCP.
Figure 5:
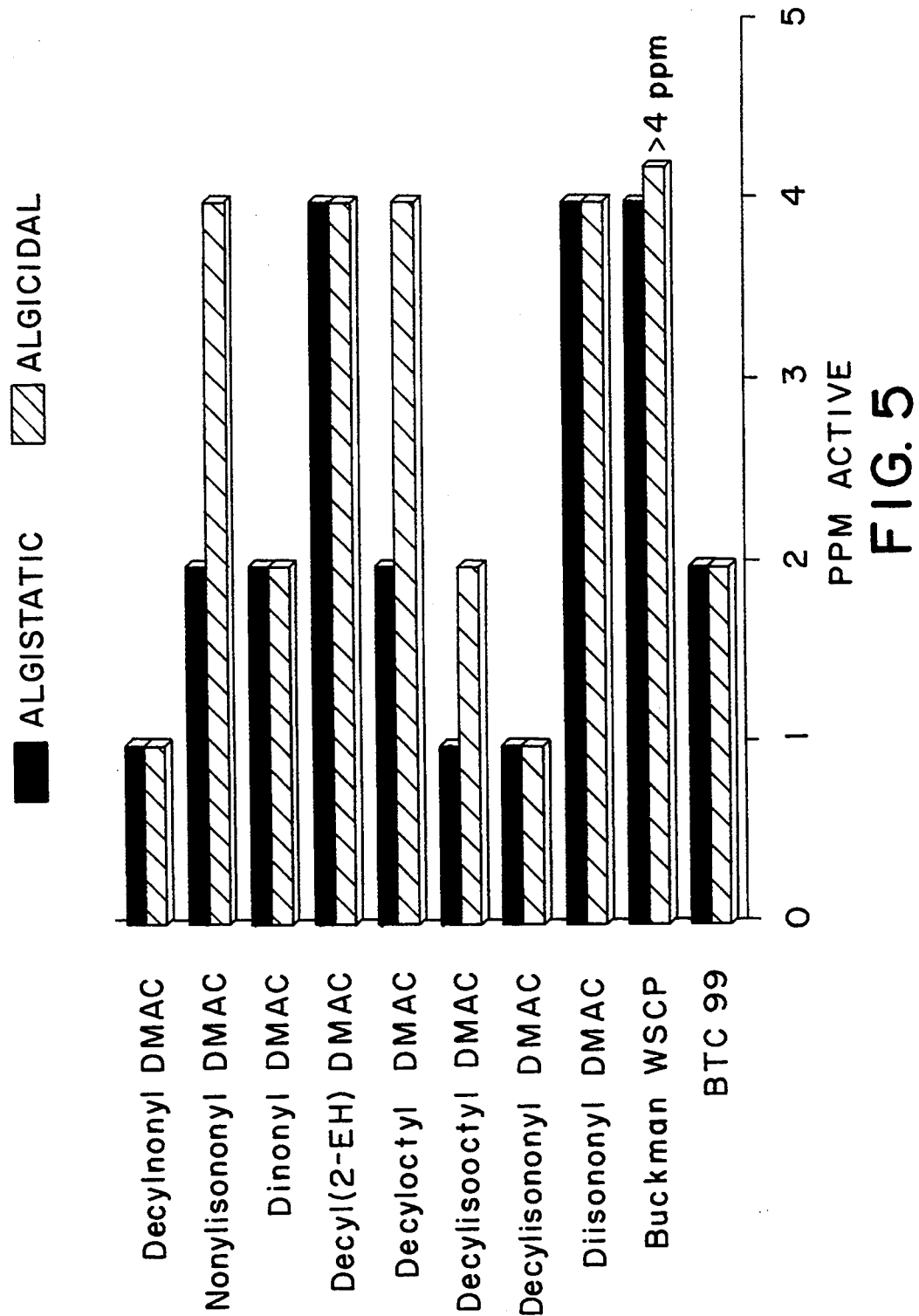
FIG. 5 illustrates an EPA pure culture test against *Phormidium luridum* (algae) at a concentration of $3.0 \times 10^5$ cells/ml. Decylnonyl DMAC and decyisononyl DMAC are compared to commercial quaternaries such as Buckman WSCP.

The results were summarized in Table 2 and FIGS. 4 and 5.

TABLE 2

EPA PURE CULTURE TEST VS. PHORMIDIUM AND CHLORELLA ALGICIDAL/ALGISTATIC EFFECT*

| Compound | Rep. | 10,000 cells/ml | | 300,000 cells/ml | |
|---|---|---|---|---|---|
| | | Primary Challenge** | Subculture** | Primary Challenge** | Subculture** |
| BTC-99 | A | 0.5 (0.5) | 1.0 (1.0) | 2.0 (0.5) | 1.0 (4.0) |
| | B | 0.5 (0.5) | 0.5 (1.0) | 2.0 (0.5) | 2.0 (4.0) |
| Buckman WSCP | A | 1.0 (1.0) | 4.0 (0.25) | 4.0 (0.5) | >4.0 (1.0) |
| | B | 1.0 (1.0) | 4.0 (0.25) | 4.0 (0.5) | >4.0 (1.0) |
| Decylnonyl DMAC | A | 0.5 (0.5) | 0.5 (2.0) | 0.5 (0.5) | 4.0 (4.0) |
| | B | 0.5 (0.25) | 0.5 (>4.0) | 1.0 (0.5) | 1.0 (>4.0) |
| Dinonyl DMAC | A | 0.5 (1.0) | 1.0 (4.0) | 1.0 (1.0) | 1.0 (4.0) |
| | B | 0.5 (1.0) | 1.0 (4.0) | 2.0 (1.0) | 2.0 (4.0) |
| Nonylisononyl DMAC | A | <0.016 (1.0) | <0.016 (2.0) | 2.0 (2.0) | 1.0 (4.0) |
| | B | <0.016 (1.0) | <0.016 (4.0) | 2.0 (2.0) | 1.0 (>4.0) |
| Decyl-2-ethyl hexyl DMAC | A | 4.0 (4.0) | 4.0 (>4.0) | 4.0 (2.0) | >4.0 (>4.0) |
| | B | 2.0 (4.0) | 4.0 (>4.0) | 4.0 (4.0) | 4.0 (>4.0) |
| Decyloctyl DMAC | A | 2.0 (1.0) | 4.0 (4.0) | 2.0 (1.0) | 4.0 (4.0) |
| | B | 1.0 (1.0) | 2.0 (>4.0) | 2.0 (1.0) | 4.0 (4.0) |
| Decylisooctyl DMAC | A | 1.0 (4.0) | 2.0 (4.0) | 1.0 (4.0) | 2.0 (>4.0) |
| | B | 1.0 (2.0) | 2.0 (4.0) | 1.0 (2.0) | 2.0 (>4.0) |
| Decylisononyl DMAC | A | 0.5 (0.5) | 1.0 (2.0) | 1.0 (0.5) | 1.0 (2.0) |
| | B | 0.5 (0.5) | 1.0 (2.0) | 1.0 (0.5) | 1.0 (2.0) |
| Diisononyl DMAC | A | 4.0 (4.0) | 4.0 (>4.0) | 4.0 (4.0) | 4.0 (>4.0) |
| | B | 4.0 (4.0) | 4.0 (>4.0) | 4.0 (4.0) | 4.0 (>4.0) |

*Test concentrations in ppm-4, 2, 1, 0.5, 0.25, 0.125, 0.063, 0.032 and 0.016
**Minimum concentrations resulted in no growth of Phormidium and Chlorella.

Of the compounds tested, the decylnonyl DMAC and decylisononyl DMAC exhibit the greatest amount of algicidal effect. The relative efficacy, in decreasing order, is decylisononyl DMAC, BTC-99, decylnonyl DMAC > Buckman WSCP > > diisononyl DMAC.

Example 4: Evaluation of Bactericidal Efficacy

The test organisms used in this study were as follows: *Pseudomonas aeruginosa, Serratia marcescens, Escherichia coli, Staphylococcus aureus*. The test conditions are described below.

One hundred microliters of filter sterilized pool water was dispensed into 96 well microliter plates (wells number 2–12). Two fold serial dilutions of various algicides, in the pool water, were made in the 96-well microliter plates to give concentrations of 64, 32, 16, 8, 4, 2, 1, 0.5, 0.25, 0.125, 0.063, and 0.0315 ppm.

Bacteria were grown overnight at 37° C., harvested by centrifugation, washed twice in 0.9% w/v NaCl and then suspended in filter sterilized pool water. 100 microliters of inoculum ($3.0 \times 10^5$ cells) were added to each well and the plates were incubated at 37° C.

Figure 3:
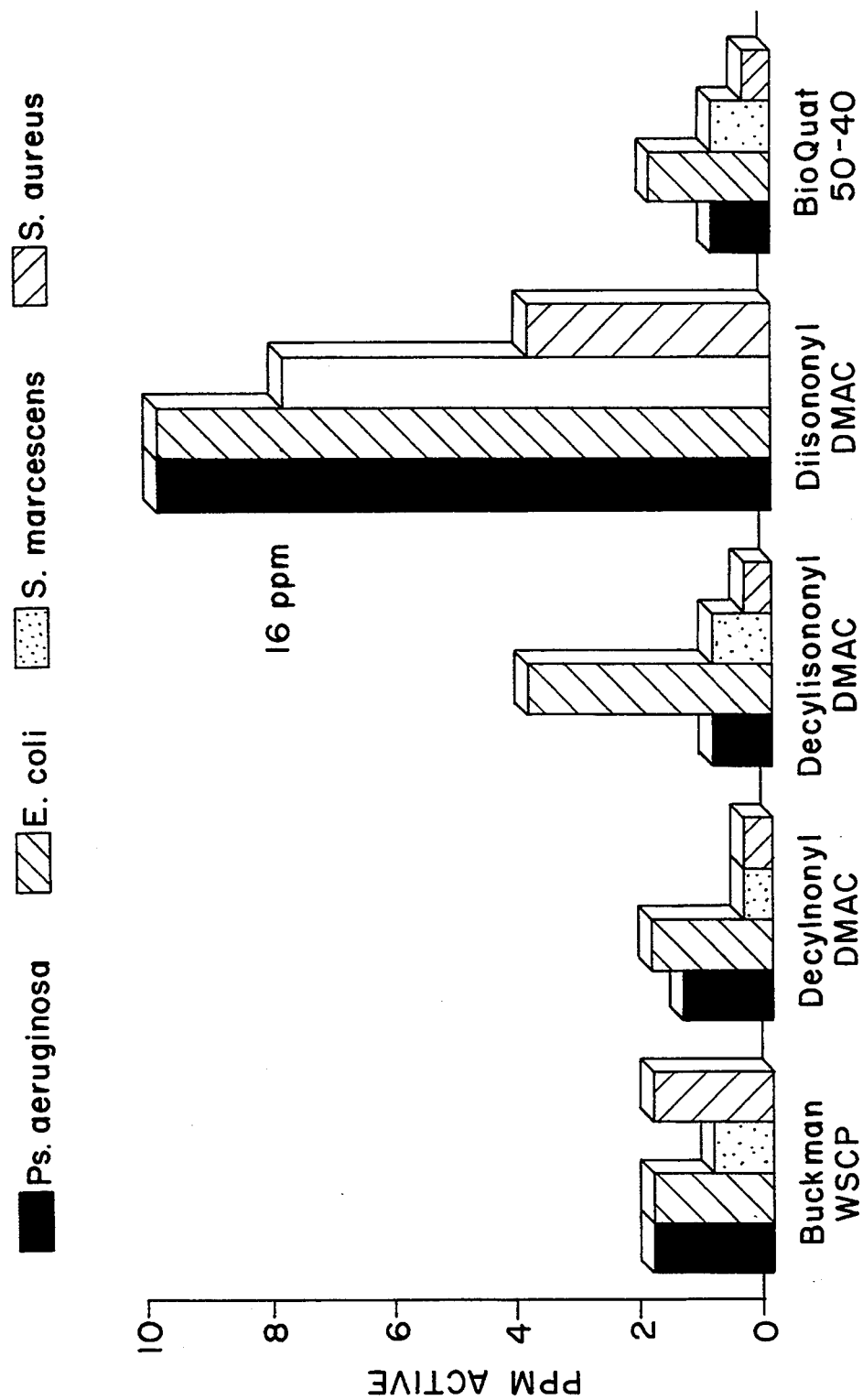
FIG. 3 illustrates the MIC required to inhibit the growth of bacteria such as *Pseudomonas aeruginosa, Escherichia coli, Serratia marcescens,* and *Staphylococcus aureus.* Decylnonyl and decylisononyl DMAC are compared to diisononyl DMAC and commercial quaternaries such as Buckman WSCP and Bio-Quat 50-40.

After 24 hours of incubation, 20 microliters of a 10x solution of sterile Tryptic Soy Broth was added to each well. The plates were then incubated for another 24 hours at 37° C. The lowest concentration was recorded and summarized in Table 3 and illustrated in FIG. 3.

TABLE 3

BACTERICIDAL EFFICACY STUDY-MIC*

| COMPOUND | Ps. aeruginosa | E. coli | S. marcescens | S. aureus |
|---|---|---|---|---|
| Decylnonyl DMAC | 0.5 | 2 | 0.5 | 0.5 |
| Decylisononyl DMAC | 1 | 4 | 1 | 0.5 |
| Diisononyl DMAC | 16 | 16 | 8 | 4 |
| Buckman WSCP | 2 | 2 | 1 | 2 |
| Bio-Quat 50-40 | 1 | 2 | 1 | 0.5 |
| Bio-Quat 50-28 | 1 | 0.5 | 1 | 0.5 |

*concentration in ppm active biocide

Based on the results in Table 3, decylnonyl DMAC and decylisononyl DMAC, as well as the commercial agents, possess greater bactericidal effect relative to diisononyl DMAC. Decylnonyl DMAC appears to have a comparable or better bactericidal effect relative to the commercial agents.

Example 5: Decylisononyl DMAC Half-life Study in a Circulating Pool

In this example, decylisononyl DMAC was evaluated via pool half-life circulation test. The results were compared with didecyl DMAC and $H_2O_2$ as controls. The test conditions are summarized below. 1700 gallons of water was placed in a plaster pool and maintained at a temperature of 80°–85° F. and at a pH of 7.4 to 7.6. The total alkalinity was 90–130 ppm with a calcium hardness of 175–225 ppm. The initial concentration for hydrogen peroxide was 40 ppm. The initial concentration for decylisononyl DMAC and didecyl DMAC were both 34 ppm based on actives. The test results are summarized in Table 4 and FIG. 1.

TABLE 4

POOL CIRCULATION STUDY

| Time (day) | Decylisononyl DMAC | Didecyl DMAC | Hydrogen Peroxide |
|---|---|---|---|
| 0 | 100 | 100 | 100 |
| 4 | 76.5 | 64.7 | 3.0 |
| 6 | 35.3 | 29.4 | 0 |

TABLE 4-continued

POOL CIRCULATION STUDY

| Time (day) | Decylisononyl DMAC | Didecyl DMAC | Hydrogen Peroxide |
|---|---|---|---|
| 11 | 35.3 | 29.1 | 0 |

The results indicate that the half-life of decylisononyl DMAC is 5.3 days for didecyl DMAC and less than 3 days for hydrogen peroxide.

Example 6: Circulation Foam Testing

This test was performed on decylnonyl DMAC, decylisononyl DMAC, decylisononyl DMAA and decylisononyl DMAB using a circulation foam test apparatus and the results were compared with Barquat MB-50 and Buckman WSCP.

For this test, two liters of each sample containing 15 ppm active biocides were prepared in the test apparatus and circulated from the bottom and back into the top of the 4 liter buret.

Figure 6:
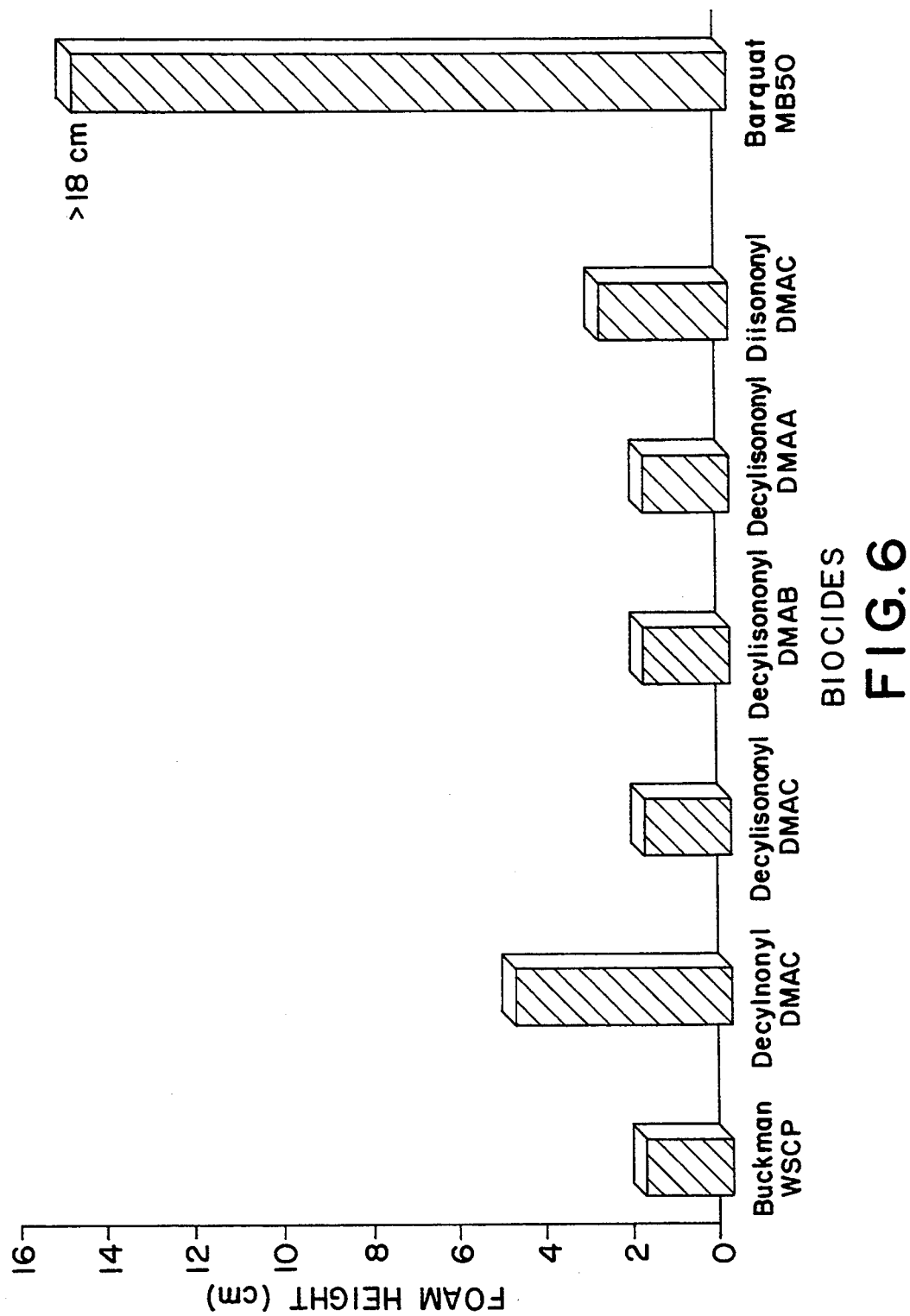
FIG. 6 illustrates a circulation foam test at a biocide concentration of 15 ppm based on actives. The foam height generated by decylisononyl DMAC, decylisononyl DMAB (dimethylammonium bromide) and decylisononyl DMAA (dimethylammonium acetate) are compared to a diisononyl DMAC and commercial quaternaries such as Buckman WSCP and Barquat MB-50.

For each sample, the foam height generated were recorded after the first 10 minutes. Readings were recorded every thirty minutes until four consecutive recordings agree. This value is recorded as the equilibrium foam height. The results are summarized in Table 5 and FIG. 6.

TABLE 5

CIRCULATION FOAM TEST

| Compound | Equilibrium Foam Height (cm) |
|---|---|
| Decylnonyl DMAC | 5 |
| Decylisononyl DMAC | 2 |
| Decylisononyl DMAB | 2 |
| Decylisononyl DMAA | 2 |
| Diisononyl DMAC | 3 |
| Barquat MB-50 | 18 |
| Buckman WSCP | 2 |

Barquat MB-50 at 15 ppm active had a foam height significantly higher than any of the quarternaries tested. It was more than three times higher than the other compounds tested. Decylnonyl DMAC has a foam height of 5 cm. The remaining compounds tested, i.e., decylisononyl DMAC, decylisononyl DMAB, decylisononyl DMAA, diisononyl DMAC and Buckman WSCP, had almost no foam at 15 ppm quat concentration.

Example 7: Modified Swimming Pool Disinfectant Test

Decylnonyl DMAC, dinonyl DMAC, nonylisononyl DMAC, decyl-2-ethylhexyl DMAC, decyloctyl DMAC, decylisooctyl DMAC, decylisononyl DMAC and diisononyl DMAC were evaluated in *E. coli.* (ATCC #11229) using a modified AOAC test for "Disinfectants (water) for Swimming Pools" in "Official Methods of Analysis of the Association of Official Analytical Chemists," Fourteenth Edition, 1984; Sidney Williams, editor; published by the Association of Official Analytical Chemists, Inc., 1111 North Fourteenth Street, Suite 210, Arlington, Va., 22209, pp. 75–77. The biocide concentrations tested were 5, 10, and 15 ppm.

TABLE 6

SWIMMING POOL DISINFECTANT TEST

| Compound | Active ppm | Plate counts* after exposure times of | | | |
|---|---|---|---|---|---|
| | | 30 sec | 1 min | 5 min | 10 min |
| Decyl- nonyl DMAC | 5 | 340 | 0 | 0 | 0 |
| | 10 | 0 | 0 | 0 | 0 |
| | 15 | 0 | 0 | 0 | 0 |
| Dinonyl DMAC | 5 | TNC** | TNC | 112 | 55 |
| | 10 | TNC | 15 | 0 | 0 |
| | 15 | 0 | 0 | 0 | 0 |
| Nonyl- isononyl DMAC | 5 | TNC | TNC | TNC | TNC |
| | 10 | TNC | TNC | 55 | 34 |
| | 15 | 320 | 120 | 15 | 4 |
| Decyl- octyl DMAC | 5 | TNC | TNC | TNC | TNC |
| | 10 | TNC | TNC | 185 | 65 |
| | 15 | 320 | 0 | 0 | 0 |
| Decyl- isooctyl DMAC | 5 | TNC | TNC | TNC | TNC |
| | 10 | TNC | TNC | TNC | TNC |
| | 15 | TNC | TNC | 2630 | 360 |
| Decyl- isononyl DMAC | 5 | TNC | 900 | 5 | 4 |
| | 10 | 0 | 0 | 2 | 0 |
| | 15 | 240 | 0 | 0 | 0 |
| Bio-Quat 50-40 | 5 | 750 | 3 | 0 | 2 |
| | 10 | 0 | 0 | 0 | 0 |
| | 15 | 0 | 0 | 0 | 0 |

*The number control count was 157 × 10⁴
**TNC = Too numerous to count

The results, shown in Table 6, indicated that decylnonyl DMAC and decylisononyl DMAC all have activity comparable to Bio-Quat 50-40.

Example 8: Evaluation of Molluscicidal Efficacy Against Corbicula Fluminea

Decylisononyldimethylammonium compounds were evaluated against adult *Corbicula fluminea*, asiatic clam. The results were compared with Buckman WSCP. Fresh water was obtained from Spruce Run reservoir in New Jersey. A total of 20 1-liter test beakers were set up, each containing 400 ml of heavily aerated biocide solutions. The four biocides are decylisononyl DMAC (chloride), decylisononyl DMAA (acetate) and decylisononyl DMAB (bromide) and Buckman WSCP, each at concentrations of 100, 50, 10, 5 and 1 ppm based on actives. Ten adult asiatic clams, each between 1 and 1½ inch in shell length, are added to each of the test breakers as well as to two control beakers containing only heavily aerated fresh water. Only clams which are definitely alive are used in the test. The asiatic clams are observed daily signs of life. The results were recorded after 72 hours of exposure time to the test solution, and summarized in Table 7.

TABLE 7

MOLLUSCICIDAL EFFICACY TEST AGAINST ASIATIC CLAMS*

| Biocide Concentration | 100 ppm | 50 ppm | 10 ppm | 5 ppm | 1 ppm | 0 ppm (control) |
|---|---|---|---|---|---|---|
| Decyliso- nonyl DMAC | 0 | 0 | 0 | 0 | 10 | |
| Decyliso- nonyl DMAA | 0 | 0 | 0 | 0 | 10 | |
| Buckman WSCP | 2 | 2 | 10 | 9 | 10 | |
| Control 1 | — | — | — | — | — | 10 |
| Control 2 | — | — | — | — | — | 10 |

*number of claims alive at the end of 72 hr.

The results show that decylisononyldimethylammonium compounds are more effective than Buckman WSCP as molluscicides against asiatic clams. At a 5 ppm biocide concentration, asiatic clams were completed killed by decylisononyldimethylammonium compounds in three days.

Example 9: Evaluation of Molluscicidal Efficacy Against Zebra Mussels

Various formulations of decylnonyl DMAC and decylisononyl DMAC, as described in Example 4, are dissolved in beakers containing 100 ml of heavily aerated tap water. Ten adult zebra mussels from Lake Michigan, each between 2 mm and 10 mm in shell length, are added to each of the test beakers as well as to two control beakers containing only heavily aerated tap water. The water is changed daily throughout the test period. Only mussels which are definitely alive (feeding) are used in the test. The zebra mussels are observed daily for signs of life. After three days (96 hours), the majority of the mussels are killed.

What is claimed is:

1. A method of controlling bacteria in an aqueous solution which comprises exposing said bacteria to an effective amount of a biocidal qauaternary ammonium compound having the structural formula:

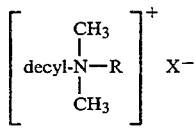

wherein X is chloride, bromide, iodide, or alkyl carboxylate anion having a $C_1$–$C_{18}$ alkyl radical, and R is n-nonyl or isononyl.

2. The method according to claim 1, wherein the ammonium compound is decylnonyldimethylammonium chloride, decylisononyldimethylammonium chloride, or mixtures thereof.

3. A method of controlling algae in an aqueous solution which comprises exposing said algae to an effective amount of a biocidal quaternary ammonium compound having the structural formula:

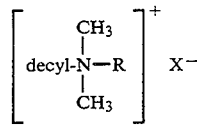

wherein X is chloride, bromide, iodide, or alkyl carboxylate anion having a $C_1$–$C_{18}$ alkyl radical, and R is n-nonyl or isononyl.

4. The method according to claim 3, wherein the ammonium compound is decylnonyldimethylammonium chloride, decylisononyldimethylammonium chloride, or mixtures thereof.

5. A method of controlling molluscs in an aqueous solution which comprises exposing said molluscs to an effective amount of a biocidal quaternary ammonium compound having the structural formula:

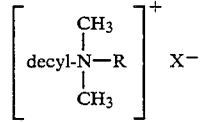

wherein X is chloride, bromide, iodide, or alkyl carboxylate anion having a $C_1$–$C_{18}$ alkyl radical, and R is n-nonyl or isononyl.

6. The method according to claim 5, wherein the ammonium compound is decylnonyldimethylammonium chloride, decylisononyldimethylammonium chloride, or mixtures thereof.

* * * * *